United States Patent [19]
Goldfarb

[11] Patent Number: 5,951,590
[45] Date of Patent: Sep. 14, 1999

[54] SOFT TISSUE SUTURE ANCHOR

[76] Inventor: Michael A. Goldfarb, 409 Little Silver Point Rd., Little Silver, N.J. 07739

[21] Appl. No.: 09/094,150

[22] Filed: Jun. 9, 1998

[51] Int. Cl.$^6$ .................................................. A61B 17/04
[52] U.S. Cl. ........................... 606/232; 606/157; 606/216
[58] Field of Search ................................... 606/157, 216, 606/232, 151

[56] References Cited

U.S. PATENT DOCUMENTS

| | | |
|---|---|---|
| 3,753,438 | 8/1973 | Wood et al. . |
| 3,857,396 | 12/1974 | Hardwick . |
| 3,910,281 | 10/1975 | Kletschka et al. . |
| 3,976,079 | 8/1976 | Samuels et al. . |
| 4,291,698 | 9/1981 | Fuchs et al. . |
| 4,387,489 | 6/1983 | Dudek . |
| 4,750,492 | 6/1988 | Jacobs . |
| 4,969,892 | 11/1990 | Burton et al. . |
| 5,078,731 | 1/1992 | Hayhurst . |
| 5,282,832 | 2/1994 | Toso et al. . |
| 5,330,442 | 7/1994 | Green et al. . |
| 5,409,499 | 4/1995 | Yi ........................................... 606/151 |
| 5,474,572 | 12/1995 | Hayhurst . |
| 5,514,159 | 5/1996 | Matula et al. . |
| 5,810,853 | 9/1998 | Yoon ...................................... 606/151 |

*Primary Examiner*—Gary Jackson
*Attorney, Agent, or Firm*—Duane, Morris & Heckscher, LLP

[57] ABSTRACT

The present invention provides a suture anchor comprising a plate having a tissue abutting surface and including a centrally defined bore sized to accept at least one strand of suture therethrough. A suture support is provided comprising a first suture gripping member connected to the plate and positioned adjacent the centrally defined bore on the side of the plate remote from the tissue abutting surface, and a second suture gripping member mounted on a deformable support connected to the first suture support and movable into engagement with the first suture support by deforming the deformable support. The first and second suture supports have irregular cooperating engaging surfaces which grip a suture between them when the surfaces are engaged. Advantageously, first and second gripping members form a suture crimp that is disposed in spaced relation to the plate, and in generally confronting relation to the bore, both before and after the crimping of the suture. This arrangement maintains the point of gripping of the suture distant from the point of exit from the tissue portions being sutured. This spaced and generally confronting arrangement between the suture crimp and the plate 10 helps to minimize damage to the tissue caused by movement of the suture relative to the tissue during suturing and afterward. Also, this advantageous arrangement also provides for more accurate location of the suturing point in the tissue when that site is viewed in a subsequent radiographic image.

16 Claims, 4 Drawing Sheets

SOFT TISSUE SUTURE ANCHOR

BACKGROUND OF THE INVENTION

1. Field of the Invention

The invention generally relates to the field of fastening devices for use in surgical procedures, and in particular concerns suture anchors for use in laparoscopic and arthroscopic surgery.

2. Prior Art

Sutures are commonly used to close incisions and to reunite damaged tissue. Typically, the sutures are passed through the tissue and the free ends of the sutures are tied together. In many instances, the suturing site is exposed to an extent sufficient to permit the surgeon to quickly tie the suture by hand. However, in some procedures such as laparoscopic or arthroscopic surgery, the suturing site is inaccessible by hand. As a result, the surgeon may be required to tie the suture ends into a knot at a location remote from the suture site, and then manipulate suitably configured instruments for sliding the knot to the site.

For example, laparoscopic surgical procedures usually employ a small diameter cannula that extends through a small incision made in the body of a patient (often the abdomen). The suture extends from the suturing site through the cannula. The exposed free ends of each suture are tied by the surgeon and the knot is slid through the cannula to the suturing site. The operating instruments have relatively long and narrow portions which are inserted through a cannula to perform the operation in the interior of the body. The instrumentation for such procedure is actuated from outside the body. It can readily be understood that the dexterity required to tie free suture ends under such conditions not only places a burden upon the operating personnel, but also poses a greater risk to the patient.

Various suture clips and suture anchors have been provided in the prior art for solving these and other such problems. For example, U.S. Pat. No. 5,078,731 to Hayhurst discloses a suture clip for engaging one or more sutures having an upper leg and an opposing lower leg that are joined at a flexible hinge. The clip is formed from a resilient material that normally biases the clip toward an open position. The Hayhurst suture clip is slidable along the suture(s) when it is in its open position. When positioned at the suturing site, the Hayhurst clip may be closed and the upper and lower legs latched to one another to fix the position of the clip, thereby securing the suture(s). Several days or weeks after surgery suture clips of this type are often difficult to identify by conventional radiographic techniques. Also, the point of fixation along the suture is normally located immediately adjacent to the tissue being sutured. In some instances, this can lead to undesirable abrading of the tissue as the clip and tissue move relative to one another. Also, this type of clip may have a tendency to "dig" into the adjoining tissue or "angulate" thereby allowing the clip to erode into immediately underlying tissue, causing a weakening of the tissue which could lead to complications during recovery. Also, devices such as Hayhurst's are often quite difficult to manipulate and to close onto a suture intracorporeally during laparoscopic surgical procedures.

In U.S. Pat. No. 4,291,698 to Fuchs, et al., a button-type suture retainer is disclosed for use in closing wounds in the epidermis. Fuchs' suture-retainer includes a disk having a slot which extends to a passageway adapted for guiding a suture through the circumference of the disk. The passageway is sealed by clamping a flexible latching device that is formed integral with the slotted disk and adapted for clamping a suture in the passageway. The latching device includes a disk segment that is movable parallel with the slotted disk, over the slot and passage, to a latched position where its inner marginal part is past the passageway. The suture is gripped and held by friction and compression. The disk and the disk segment are connected, via a flexible hinge, so that the button can be handled as a unit. Fuchs et al.'s slotted disk aids in the prevention of damage to skin, however, its latching mechanism and structural size and arrangement are such that it must be manipulated by one hand, and is not, therefore, suitable for laparoscopic surgical procedures. Also, since this type of button anchor requires an integral flexible hinge, it is often very difficult to form from sufficiently radiopaque material to make post operative location of the device by radiographic imaging trouble free.

Other suture fixation devices are disclosed in U.S. Pat. Nos. 3,753,438 issued Aug. 21, 1973 to Wood et al.; 3,857,396; 3,910,281; 3,976,079 issued Aug. 24, 1976 to Samuels et al.; 4,387,489 issued Jun. 14, 1983 to Dudek; 4,750,492 issued Jun. 14, 1988 to Jacobs; 4,969,892 issued Nov. 13, 1990 to Burton et al.; 5,282,832 issued Feb. 1, 1994 to Toso et al; 5,474,572 issued Dec. 12, 1995 to Hayhurst; 5,409,499 issued Apr. 25, 1995 to Yi; and 5,514,159 issued May 7, 1996 to Matula et al.

While the foregoing devices perform the function of suture retention, there is a need for an improved suture retainer clip which is simple in construction, easy to apply, and readily usable in laparoscopic or arthroscopic surgical procedures. There is a further need for a soft tissue suture anchor that evenly distributes the tensile load (applied to it during suturing) across a relatively large portion of the adjoining tissue so that abrasion and "digging-in" are much less likely to occur. There is also a need for a suture retention clip that allows for easy post-operative location and orientation, via radiological means. In particular, with a radiopaque suture clip, a surgeon can assess the integrity or disruption of a sutured tissue juncture.

SUMMARY OF THE INVENTION

The present invention provides a suture anchor comprising a plate having a tissue abutting surface and including a centrally defined bore sized to accept at least one strand of suture therethrough. A suture support is provided comprising a first suture gripping member connected to the plate and positioned adjacent the centrally defined bore on the side of the plate remote from the tissue abutting surface, and a second suture gripping member mounted on a deformable support connected to the first suture support and movable into engagement with the first suture support by deforming the deformable support. The first and second suture supports have irregular cooperating engaging surfaces which grip a suture between them when the surfaces are engaged. Advantageously, first and second gripping members form a suture crimp that is disposed in spaced relation to the plate, and in generally confronting relation to the bore, both before and after the crimping of the suture. This arrangement maintains the point of gripping of the suture distant from the point of exit from the tissue portions being sutured. This spaced and generally confronting arrangement between the suture crimp and the plate 10 helps to minimize damage to the tissue caused by movement of the suture relative to the tissue during suturing and afterward. Also, this advantageous arrangement also provides for more accurate location of the suturing point in the tissue when that site is viewed in a subsequent radiographic image.

The present invention is also directed to a method of tying surgical sutures which comprising the steps of: positioning a suture anchor having a plate having a tissue abutting surface and including a centrally defined bore sized to accept at least one strand of suture therethrough, suture support comprising a first suture gripping member connected to the plate and positioned adjacent the centrally defined bore on the side of the plate remote from the tissue abutting surface, and a second suture gripping member mounted on a deformable support connected to the first suture support and movable into engagement with the first suture support by deforming the deformable support, wherein the first and second suture supports have irregular cooperating engaging surfaces which grip a suture between them when the surfaces are engaged, on one side of tissues to be sutured; mechanically gripping one end of a suture in the anchor; suturing the tissues together; positioning a second suture anchor on the other side of the tissues to be sutured; pulling the suture to a desired tension with the first and second suture anchors abutting the tissues; and mechanically gripping the free end of the suture in the second suture anchor.

BRIEF DESCRIPTION OF THE DRAWINGS

These and other objects, features and advantages of the present invention will be more fully disclosed in, or rendered obvious by, the following detailed description of the preferred embodiment of the invention, which is to be considered together with the accompanying drawings wherein like numbers refer to like parts and further wherein.

DETAILED DESCRIPTION OF THE PREFERRED EMBODIMENTS

The following description of the preferred embodiments of the invention are intended to be read in connection with the foregoing drawings and are to be considered a portion of the entire written description of this invention. As used in the following description, the terms "horizonal", "vertical", "left", "right", "up", and "down", as well as adjectival and adverbial derivatives thereof (e.g., "horizontally", "rightwardly", "upwardly", etc.) simply refer to the orientation of the structure of the invention as it is illustrated in the particular drawing figure when that figure faces the reader. Similarly, the terms "inwardly" and "outwardly" generally refer to the orientation of a surface relative to its axis of elongation, or axis of rotation, as appropriate. Also, the terms "connected" and "interconnected," when used in this disclosure to describe the relationship between two or more structures, means that such structures are secured or attached to each other either directly or indirectly through intervening structures, and includes pivotal connections.

The term "operatively connected" means that the foregoing direct or indirect connection between the structures allows such structures to operate as intended by virtue of such connection.

Figure 1:
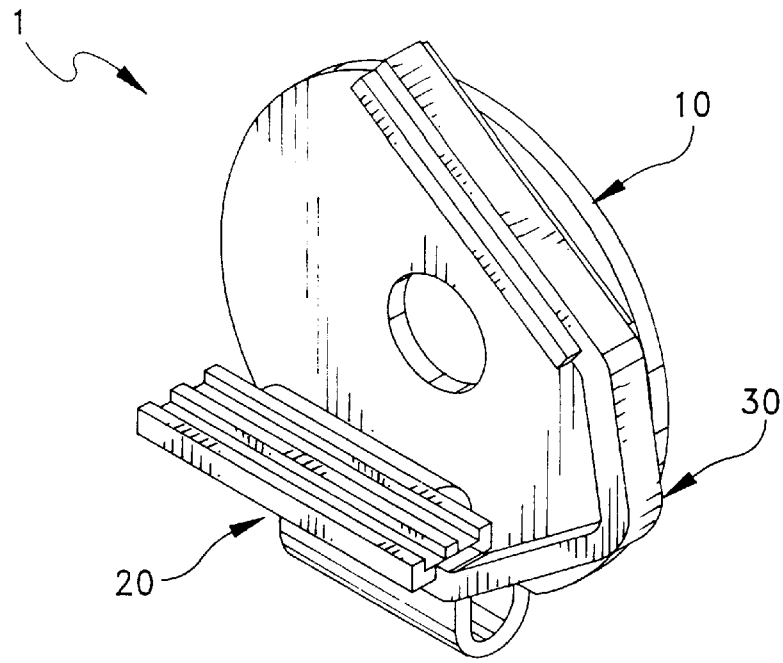
FIG. 1 is a perspective view of a soft tissue suture anchor formed in accordance with a preferred embodiment of the present invention.
Figure 2:
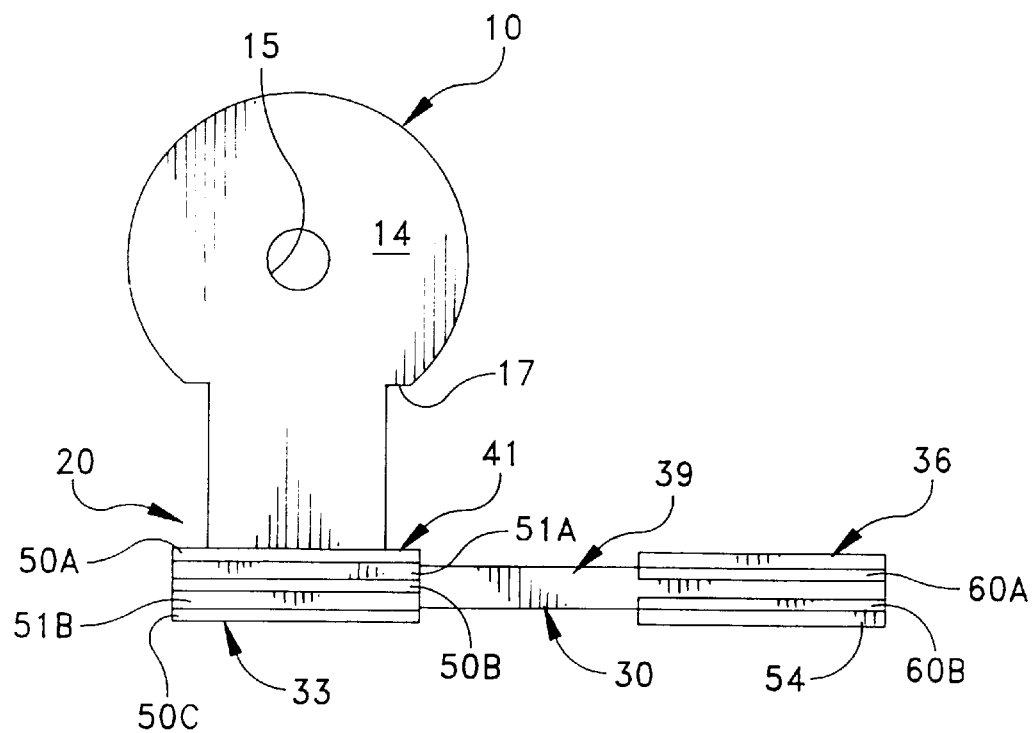
FIG. 2 is a front facing plan view of the suture anchor shown in FIG. 1, flattened out, and prior to final forming.
Figure 3:
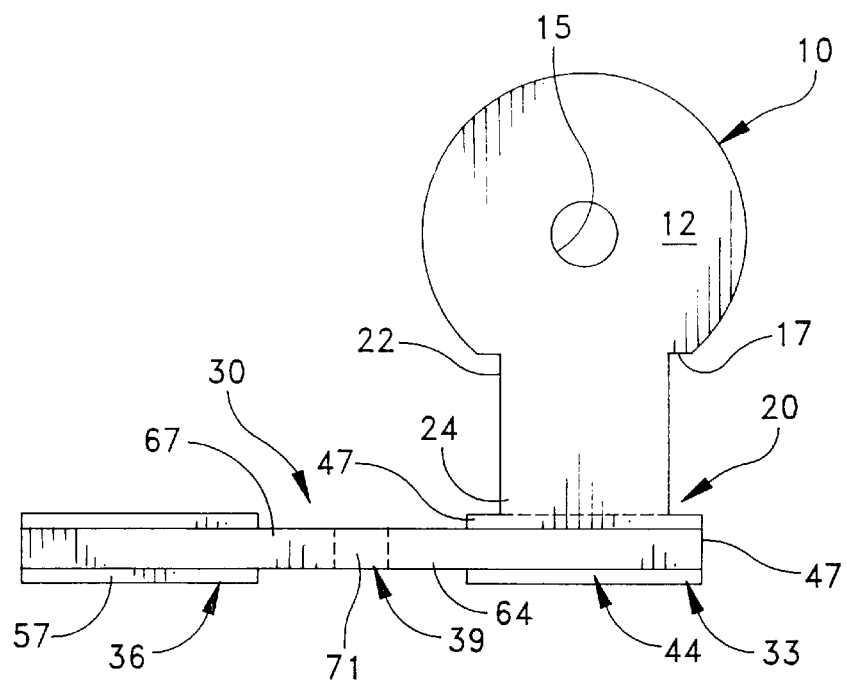
FIG. 3 is a rearwardly facing plan view of the suture anchor shown in FIG. 2.
Figure 4:
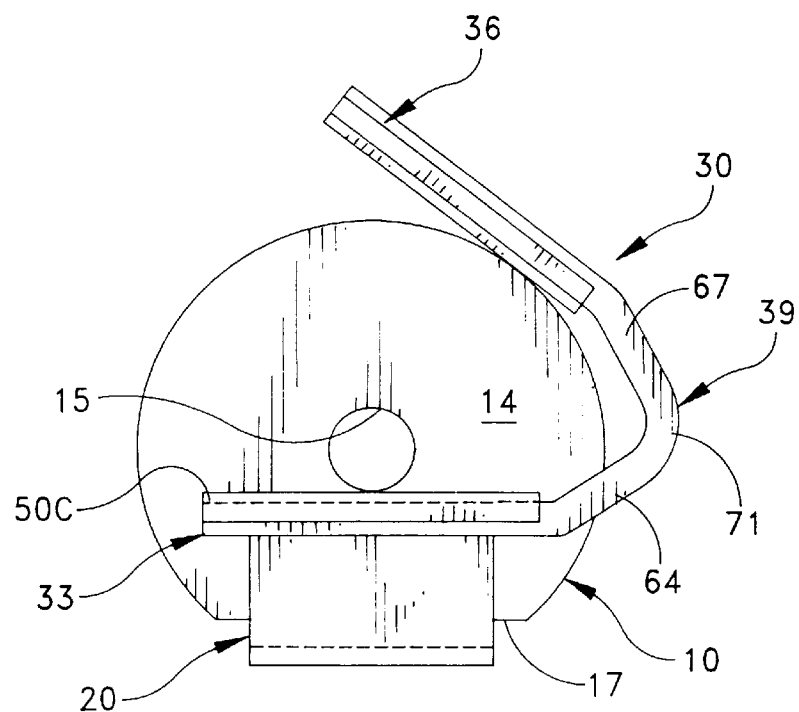
FIG. 4 is a front elevational view of the suture anchor shown in FIG. 1.

Referring to FIG. 1, a suture anchor 1 formed according to a preferred embodiment of the present invention includes a soft tissue interface plate 10, a suture pedestal 20, and a suture crimp 30. More particularly, soft tissue interface plate 10 comprises a circular disk having a tissue side 12 (FIG. 3), a crimp side 14, a centrally disposed through bore 15, and a chordal edge 17. Interface plate 10 is preferably about 0.371 inches in diameter and approximately 0.015 inches thick. Bore 15 is about 0.078 inches, and generally circular in shape. Chordal edge 17 extends chordally across a side portion of plate 10, and is approximately 0.187 inches in width. Soft tissue interface plate 10 may have other shapes, e.g., elliptical or oval, as long as the use of such shapes does not include sharp edges or protrusions which would damage the soft tissue located adjacent to side 12. Also, interface plate 10 is formed from a radiopaque, biocompatable material, such as one of the well known titanium based alloys.

Suture pedestal 20 comprises a formable rectangular plate having a thickness similar to that of soft tissue interface plate 10 and a width of approximately 0.187 inches. Suture pedestal 20 includes a proximal end 22 and a distal end 24. Proximal end 22 of suture pedestal 20 projects outwardly from chordal edge 17 of soft tissue interface plate 10. Distal end 24 is adapted to support a suture crimp 30, as will hereinafter be disclosed in future detail.

Figure 7:
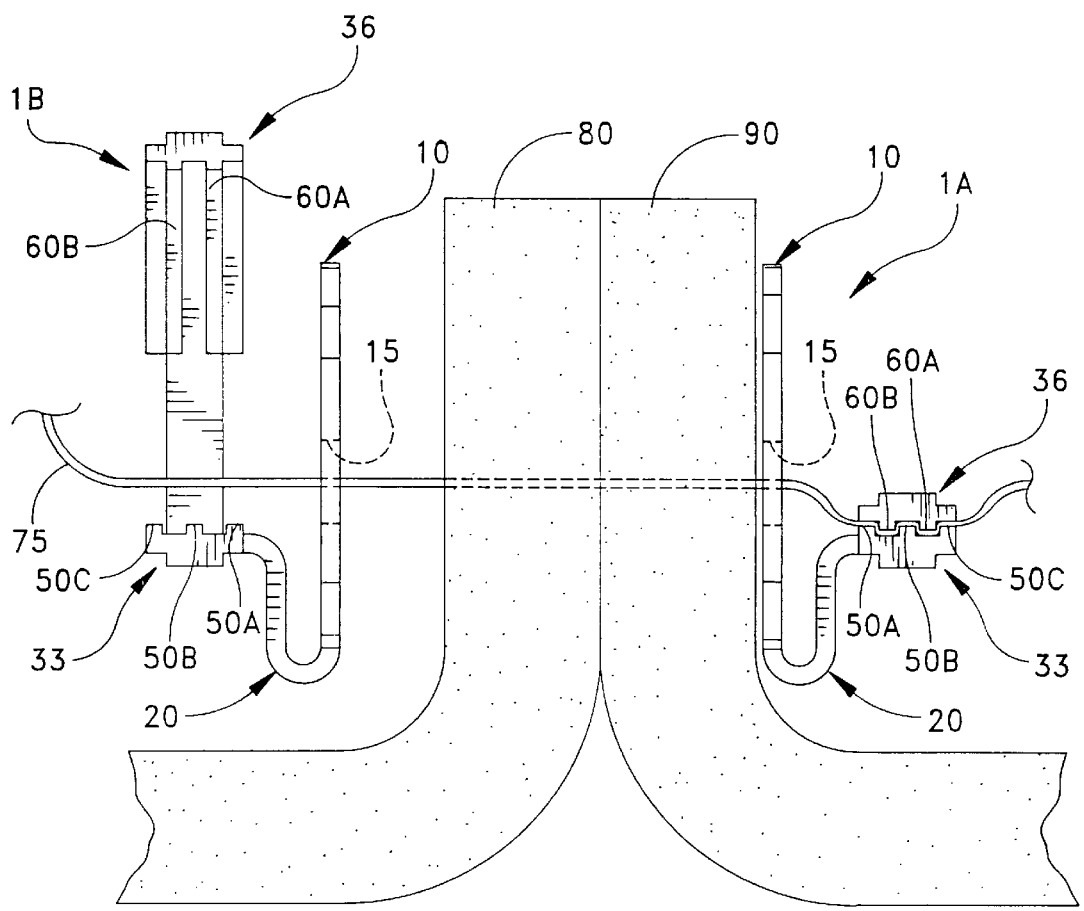
FIG. 7 is a side elevational view of the anchor and tissue shown in FIG. 6.

Suture crimp 30 comprises a lower anvil 33, an upper anvil 36 and an interconnecting arm 39. More particularly, lower anvil 33 comprises an elongate plate having an inner surface 41, an outer surface 44, and side edges 47. At least two longitudinally oriented, mutually parallel teeth project upwardly from inner surface 41. As shown in FIGS. 1, 2, 5, and 7, a preferred embodiment of the invention includes three such teeth 50A,50B,50C. Teeth 50A,50B,50C are disposed in spaced-apart parallel relation to one another so that they define between them gaps 51A and 51B that are at least the same width and depth as teeth 50A,50B,50C. Upper anvil 36 also comprises an elongate plate, similar to that of lower anvil 33, and also includes an inner surface 54 and an outer surface 57. At least one longitudinally oriented, mutually parallel tooth projects upwardly from inner surface 54. As shown in FIGS. 1, 2, 5 and 7, a preferred embodiment of the invention includes two such teeth 60A and 60B. Teeth 60A and 60B are disposed in spaced-apart parallel relation to one another so that they define between them a gap that is somewhat wider than tooth 50B of lower anvil 33. As a result of this construction, inner surfaces 41,54 complement one another. More particularly, when lower anvil 33 and upper anvil 36 are engaged with one another, tooth 50B of lower anvil 33 nests within the gap formed between teeth 60A and 60B of upper anvil 36. At the same time, tooth 50A is disposed outwardly of tooth 60A and tooth 50C is disposed outwardly of tooth 60B (FIG. 7).

Interconnecting arm 39 includes a proximal portion 64, a distal portion 67, and an elbow portion 71 integrally disposed therebetween. More particularly, proximal portion 64 of arm 39 projects outwardly from a side edge 47 of lower anvil 33. Elbow portion 71 is integral with both proximal portion 64 and distal portion 67 of arm 39 and comprise a material capable of plastically yielding in bending such that, in a bent, yielded state, elbow 71 stores elastic energy. Distal portion 67 supports upper anvil 36 along outer surface 57.

Figure 5:
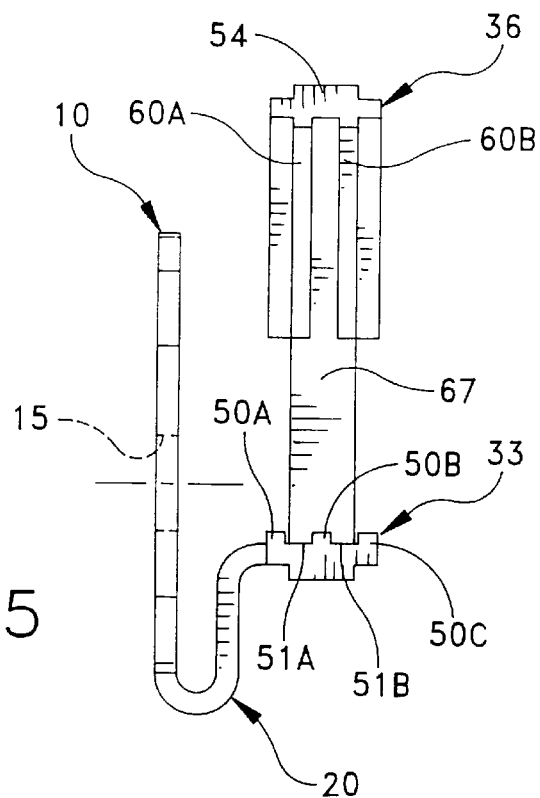
FIG. 5 is a side elevational view of the suture anchor shown in FIG. 1.

Soft tissue anchor 1 is fabricated in the following manner. Flat stock of a suitably radiopaque, deformable material, such as any of the well known biocompatable titanium based alloys, is stamped in a conventional stamping die into the configurations shown in FIGS. 2 and 3. It should be noted that teeth 50A,50B,50C and 60A and 60B may be formed in a coining operation associated with this flat stamping, or they may be skived into the material in a secondary operation in order to achieve corners sharp enough to securely engage a strand of suture 75, as will hereinafter be disclosed in further detail. Once the flat stamping is created, suture pedestal 20 is formed into a substantially "S-shaped" configuration as shown in FIG. 5. As a result of this construction, soft tissue interface plate 10 is disposed in generally perpendicular relation to side edges 47 and spaced-relation to lower anvil 33 (FIGS. 1, 5, 6, and 7). Also, suture pedestal 20 is arranged so that it may be elastically biased toward soft tissue interface plate 10, yet tend to spring back to the position shown in FIGS. 1 and 5. As such, suture pedestal 20 behaves as a compound cantilevered beam when suture crimp 30 is elastically bent toward soft tissue interface plate 10. It should be noted that as a result of this forming operation, teeth 50A,50B,50C are disposed in alignment with a bottom surface portion of bore 15. It should also be noted that suture crimp 30 is positioned in spaced-relation to soft tissue interface plate 10 by suture pedestal 20. Once suture pedestal 20 has been formed, interconnecting arm 39 is bent such that proximal portion 64 and distal portion 67 are arranged at about a 40° angle relative to one another, as shown in FIG. 1.

Figure 6:
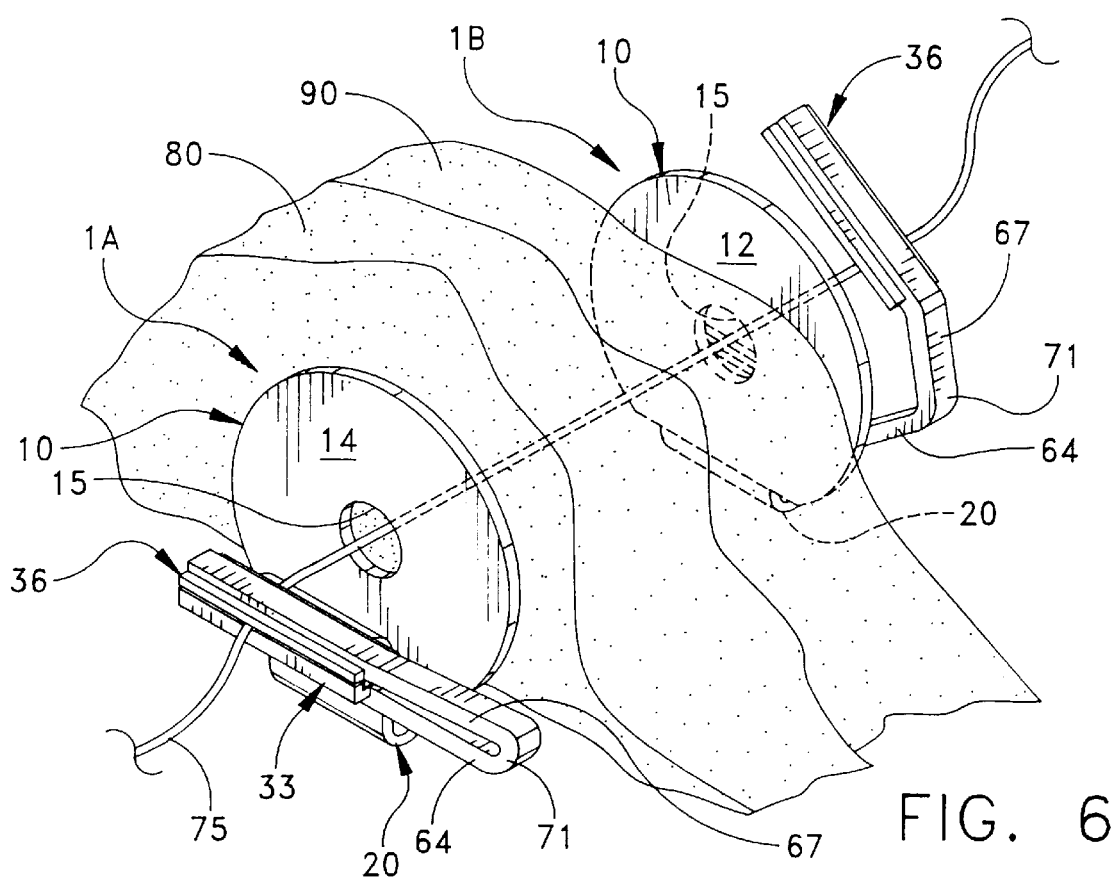
FIG. 6 is a perspective view of a portion of sectioned tissue having a suture stitch passing therethrough, with a suture anchor attached to one portion and a second suture anchor in position for clamping at a second position.

Referring to FIGS. 6 and 7, soft tissue anchor 1 is applied to sectioned tissue in the following manner. Suture 75 is first passed through adjoining first and second portions of tissue 80,90 which are to be reattached, via a conventional suturing needle or the like affixed to a free end of suture 75. Once in this position, a length of suture 75 extends from either portion of the resected tissue. A first soft tissue suture anchor 1A is then threaded onto one end of suture 75. More particularly, the free end of suture 75 is threaded through bore 15 in soft tissue interface plate 10 so as to enter bore 15 adjacent tissue side 12 of soft tissue interface plate 10, so that suture 75 exits outwardly from crimp side 14. Once soft suture tissue anchor 1A has been threaded onto suture 75, an appropriate surgical instrument is used for sliding suture anchor 1A along suture 75, through the laparoscopic cannula or the like device for gaining entry to the surgical site, and into position adjacent first portion of tissue 80. In this position, tissue side 12 of soft tissue interface plate 10 is adjacent first portion of tissue 80. Suture crimp 30 is then crimped onto suture 75.

More particularly, suture crimp 30 is grasped such that upper anvil 36 and lower anvil 33 are disposed against a suitable gripping or pinching device, e.g., forceps or other laparoscopic grasping devices. For example, one existing applicator that has been found to provide good results is the Ethicon EL-314 10 mm Hemo-clip applicator, manufactured by the Ethicon division of the Johnson & Johnson Corporation. Once in this position, suture 75 is placed over teeth 50A,50B,50C of lower anvil 33, as shown in FIG. 7. Upper anvil 36 is then moved toward lower anvil 33, and into gripping engagement with suture 75. As this occurs, elbow 71 of interconnecting arm 39 bends and plastically yields in response to upper anvil 36 being moved toward lower anvil 33. Also, as upper anvil 36 engages lower anvil 33, teeth 60A and 60B move into the gaps between teeth 50A,50B,50C, and as a result, firmly grip suture 75 therebetween. In this way, suture 75 is firmly grasped between upper anvil 36 and lower anvil 33. It will be understood that elbow 71 of interconnecting arm 39 takes a "set" after plastically yielding in response to bending, and retains upper anvil 36 in contact with lower anvil 33 with suture disposed gripped therebetween. It will also be understood that the terms "set" and "plastically yielding" are used for their common and well known meanings in mechanical design of bended beams. It will be understood that soft tissue anchor 1 may be provided "pre-crimped" to one end of a length of suture with the other end of the suture affixed to a conventional suturing needle. This arrangement allows the surgeon to immediately anchor the suture on the first pass of the suture through the tissue.

Advantageously, suture crimp 30 is disposed in spaced relation to soft tissue plate 10, and in generally confronting relation to bore 15, both before and after the crimping of suture 75. This arrangement maintains the point of gripping of suture 75 distant from the point of exit from tissue portions 80 or 90. This spaced and generally confronting arrangement between suture crimp 30 and soft tissue plate 10 helps to minimize "digging-in", side-ways "cutting", or angulation of the suture against the tissue. Also, this advantageous arrangement provides for more accurate location of the suturing point in the tissue when that site is viewed in a subsequent radiographic image.

Once the first soft tissue suture anchor 1A is positioned, a second suture anchor 1B is threaded onto the length of suture 75 that is extending from second portion of tissue 90. The previously described procedure is then followed to position the second soft tissue suture anchor 1B adjacent to second portion of tissue 90 with suture crimp 30 crimped into place on suture 75. Once in this position, further suturing rows and stitches can be made across the two portions of tissue 80,90 and further suture anchors can be positioned in either portion of tissue so as to mark various positions therealong.

It will be understood, that because of the relative placement of suture crimp 30 adjacent and spaced-away from crimp side 14 of tissue interface 10 there is little or no structure available for abrading or digging into the portion of tissue adjacent soft tissue suture anchor 1 at the point where suture 75 enters tissue portions 80,90. Also, suture 75 is maintained in a straight-line orientation relative to both suture anchors (see FIGS. 6 and 7) so that sideways pulling or cutting of the suture into the adjacent tissue is minimized. Further, when suture 75 is pulled, so that a bending load is applied to suture pedestal 20, through suture crimp 30, suture pedestal 20 tends to elastically oppose this movement, thereby applying an outwardly directed tensile bias to suture 75. Thus, as the free end of suture 75 is pulled upon by the surgeon during suturing, the crimped end of suture 75 maintains an oppositely directed tensile bias to suture 75, via cantilevered suture pedestal 20 to aid in forming tight throws in the sutured passes and knot.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

What is claimed is:

1. A suture anchor comprising a plate having a tissue abutting surface and including a centrally defined bore sized to accept at least one strand of suture therethrough, a suture support comprising a first suture gripping member connected to said plate and positioned adjacent said centrally defined bore on a side of said plate remote from said tissue abutting surface, and a second suture gripping member mounted on a deformable support connected to said first suture support and movable into engagement with said first suture support by deforming said deformable support, wherein said first and second suture supports include irregular cooperating engaging surfaces which grip said suture between them when said surfaces are engaged.

2. A suture anchor according to claim 1 wherein said first and second supports define a suture crimp disposed in spaced relation to said plate.

3. A suture anchor according to claim 1 wherein said first and second supports define a suture crimp disposed in confronting relation to said plate.

4. A suture anchor according to claim 3 wherein said first and second supports define a suture crimp disposed in spaced relation to said plate.

5. A suture anchor according to claim 4 wherein said suture crimp is disposed in confronting spaced relation to said plate both before and after crimping of a suture within said suture crimp.

6. A suture anchor according to claim 4 wherein said suture crimp maintains a point of gripping of a suture crimped therein distant from a point of exit from an adjoining tissue portions so as to minimize damage to said adjoining tissue.

7. A suture anchor according to claim 6 wherein said suture anchor provides for more accurate location of said suturing point in said adjoining tissue when that site is viewed in a subsequent radiographic image.

8. A suture anchor according to claim 1 wherein said first and second supports define a suture crimp disposed in spaced relation to said plate and supported on a pedestal that connects said suture crimp to said plate so as to maintain said suture crimp in substantially confronting relation to said bore in said plate.

9. A suture anchor comprising a suture crimp including a first suture support and a second suture support said suture supports being joined together at an end by a deformable beam for pivotal movement so that said suture supports are movable from an open state to a closed state, wherein said closed state corresponds to a substantial deforming of said beam for maintaining said first and second supports in gripping engagement with one another;

said suture supports having opposed mating surfaces that mate in said closed state to secure a suture disposed between said mating surfaces; and a tissue abutting portion interconnected with one of said two suture supports and disposed in spaced-relation to said mating surfaces, said tissue abutting portion including (i) a centrally defined through bore sized to accept at least one strand of suture therethrough (ii) a tissue interface side surface, and (iii) a crimp side surface and wherein said suture crimp is disposed in confronting relation to said crimp side surface.

10. A suture anchor according to claim 9 wherein said suture crimp is disposed in spaced relation to said crimp side surface.

11. A suture anchor according to claim 9 wherein said suture crimp is disposed in confronting spaced relation to said crimp side surface both before and after crimping of a suture within said suture crimp.

12. A suture anchor according to claim 9 wherein said suture crimp maintains a point of gripping of a suture crimped therein distant from a point of exit from an adjoining tissue portions so as to minimize damage to said adjoining tissue.

13. A suture anchor according to claim 9 wherein said suture anchor provides for more accurate location of said suturing point in said adjoining tissue when that site is viewed in a subsequent radiographic image.

14. A suture anchor according to claim 9 wherein said suture crimp is disposed in spaced relation to said crimp side surface and supported on a pedestal that connects said suture crimp to said crimp side surface so as to maintain said suture crimp in substantially confronting relation to said bore in said crimp side surface.

15. A suture anchor according to claim 9 wherein said tissue side surface comprises a substantially circular perimeter.

16. A method of tying surgical sutures which comprises the steps of:

(a) providing a suture anchor comprising a plate having a tissue abutting surface and including a centrally defined bore sized to accept at least one strand of suture therethrough, a suture support comprising a first suture gripping member connected to the plate and positioned adjacent the centrally defined bore on the side of the plate remote from the tissue abutting surface, and a second suture gripping member mounted on a deformable support connected to the first suture support and movable into engagement with the first suture support by deforming the support, the first and second suture supports having irregular cooperating engaging surfaces which grip a suture between them when the surfaces are engaged positioning a suture anchor on one side of tissues to be sutured;

(b) mechanically gripping one end of a suture in said suture anchor;

(c) suturing the tissues together;

(d) positioning a second suture anchor on the other side of the tissues to be sutured;

(e) pulling the suture to a desired tension with the first and second suture anchors abutting the tissues; and (f) mechanically gripping the free end of the suture in said second suture anchor.

* * * * *